United States Patent [19]

Cousyn et al.

[11] Patent Number: 4,591,246

[45] Date of Patent: May 27, 1986

[54] OCULAR PARAMETER MEASURING DEVICE

[75] Inventors: Bernard Cousyn, Vincennes; Ahmed Haddadi, Nogent-sur-Marne; Jean-Claude Hennequin, Congis-sur-Therouanne, all of France

[73] Assignee: Essilor International, Compagnie Generale d'Optique, Creteil, France

[21] Appl. No.: 563,559

[22] Filed: Dec. 20, 1983

[30] Foreign Application Priority Data

Dec. 22, 1982 [FR] France ................ 82 21537

[51] Int. Cl.[4] ............................. A61B 3/10
[52] U.S. Cl. .......................... 351/204; 33/200
[58] Field of Search .......... 351/204; 33/200

[56] References Cited

FOREIGN PATENT DOCUMENTS 1506352 12/1967 France .
2390751 12/1978 France .

OTHER PUBLICATIONS

C. Perrot, "Les Cristaux Liquides au Service de la Securite Routiere", Electronique & Microelectronique, No. 228, Nov. 15, 1976, pp. 39–41.

Primary Examiner—Rodney B. Bovernick
Attorney, Agent, or Firm—Charles E. Brown; Charles A. Brown

[57] ABSTRACT

A device (1) for measuring the ocular parameters of a subject is of conventional optical design, with a front panel (10), a convergent lens (11), an aiming hole (12) at the focus of the lens (11), and a light source (13) whose image in a semi-reflecting mirror (14) appears as a point at infinity. Liquid crystal matrixes are disposed in windows (15, 16, 17, 18) and controlled by a logic unit (20) connected to a control keyboard (21) and a display (22). Looking through the hole (12), the operator uses the keyboard (21) to send address signals from the logic unit (20) either to the columns of the top matrixes (15, 16) or to the lines of the top and bottom matrixes (15, 16, 17, 18). According to the operating modes selected, vertical lines appear in the top windows (15, 16) to measure the interpupillary distance or horizontal lines appear in all four windows for centering the lenses in the frame.

4 Claims, 5 Drawing Figures

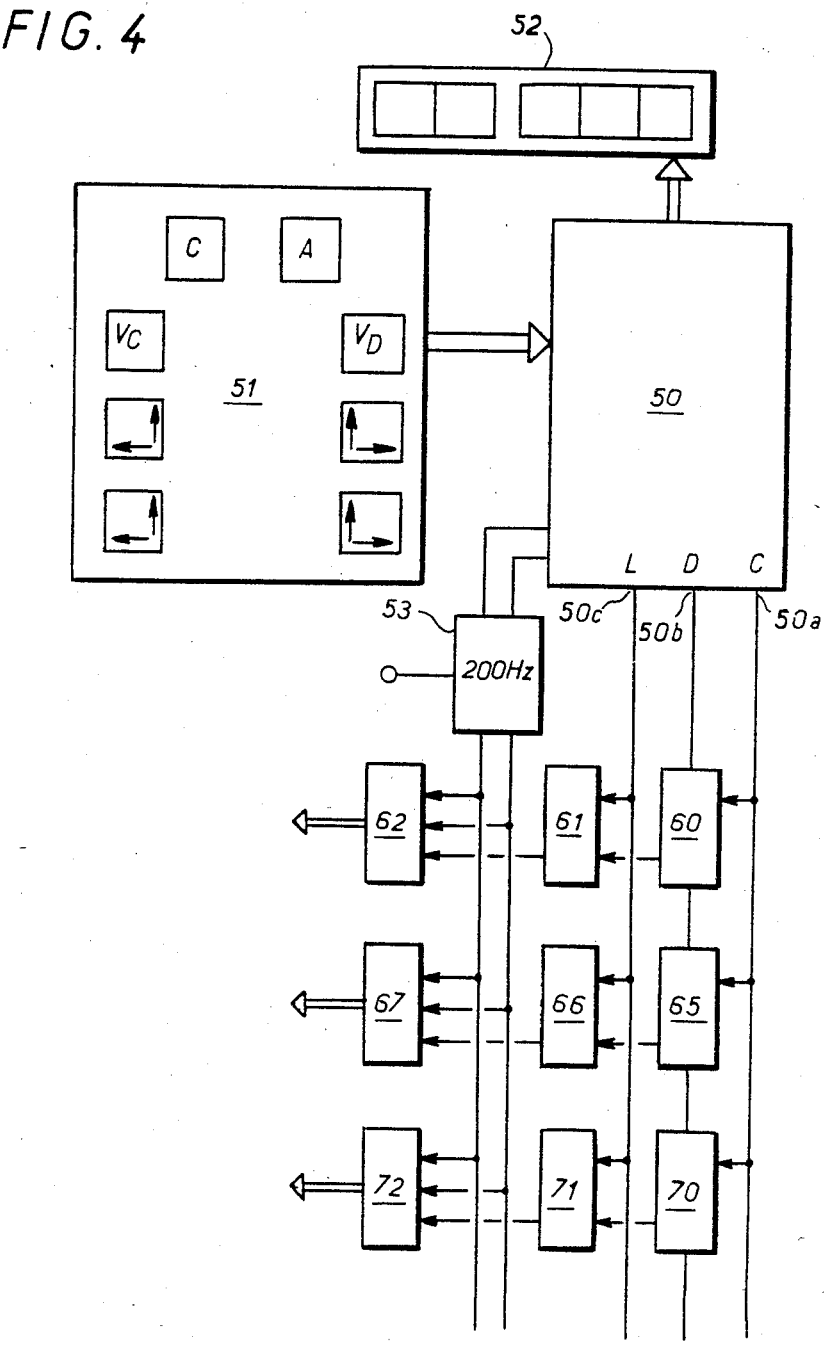

OCULAR PARAMETER MEASURING DEVICE

BACKGROUND OF THE INVENTION

1. Field of the invention

The invention concerns a device for measuring the ocular parameters of a subject, in particular the interpupillary distance, for the purpose of fitting a pair of spectacles.

2. Description of the prior art

For a pair of spectacles to suit the subject who wears them, it is necessary for the lenses to be disposed in the frame surrounds so that their principal optical axes are coincident with the optical axes of the corresponding eyes, under average conditions of use. The frame constitutes a secondary point of reference for the position of the lenses, its position relative to the face of the subject being essentially defined by the nose pads bearing on opposite sides of the nose and, as an ancillary to this, by the contact of the frame side members with the ears.

The position of the lenses relative to the frame is conveniently defined (in Cartesian coordinates with an axis of abscissae which is horizontal (with reference to the face of the subject) and a vertical axis of ordinates) by the abscissa and the ordinate of the optical center of the lens. The origin of the abscissae is naturally situated in the vertical plane of symmetry of the frame. For reasons of convenience with regard to the finishing of the lenses, there is generally taken as the origin of the ordinates the horizontal straight line which passes through the bottom part of the frame surrounds, so that the ordinate is the distance between the optical center of the lens and its bottom edge.

The interpupillary distance is the distance which separates the optical axes of the eyes when the gaze is focused at infinity. The (vector) difference between the abscissae of the optical centers of the lenses must correspond to the subject's interpupillary distance.

French patent No. 1 506 352, filed Aug. 4 1966, describes an improved device for measuring the interpupillary distance by determining for each eye the position of the reflection on the cornea of a light spot situated at infinity, with the gaze focused at infinity. Similar measurements are obtained with the gaze focused on a point at a finite distance, in which case the optical axes of the eyes converge.

According to the aforementioned patent, the device essentially comprises a box in which there are placed a lens adapted to be moved parallel to itself along its principal optical axis, a light source at the focus of the lens when the latter is at an origin farthest removed from the source, the latter being geometrically offset from the optical axis by means of a semi-reflecting mirror disposed at 45°, and on two respective opposite sides of the box perpendicular to the optical axis of the lens, a hole situated on the optical axis at the focus of the lens when at the origin, and a front plate comprising nose pads and two openings to simulate a spectacle frame, the openings surrounding the intended position of the lenses and being fitted with movable markers constituting a graticule. For purposes of measurement the movable markers and the reflections of the point source on the corneas, as seen through the hole, are rendered coincident. The position of the lens defines for the subject an effective viewing distance from the point source, whereas the operator looks through the hole which is at a point which is optically coincident at the point source at all times. Measurement of the interpupillary distance for a convergent gaze focused on a close virtual point does not introduce any angular parallax error, and the position of the graticule in the plane of the windows, which corresponds to the general plane of the lenses, defines the required position for the optical center of the lenses.

This device, which is of excellent design from the optical point of view, suffers from imperfections in the mechanical part controlling displacement of the graticules. The required accuracy of a few tenths of a millimeter imposes the use of micrometer screws or racks to move the indexes, resulting in a fragile device which must be operated slowly. Reading the position with verniers or drums associated with linear scales becomes difficult as soon as the accuracy required is greater than one-half-millimeter. Also, movement of the graticules in two mutually perpendicular directions seriously complicates the mechanical control and display devices. In point of fact, the device described in the aforementioned patent has only horizontally movable indexes, principally for determining the interpupillary distance, and as an ancillary to this for measuring the distance from the spectacle frame to the eye, by viewing from the side.

An object of the invention is a device for measuring optical parameters capable of rapidly providing accurate data for fitting lenses in a spectacle frame to the ocular parameters of a subject.

Another object of the invention is a device of this kind which provides, in addition to the distance between the pupils and between each pupil and the axis of symmetry of the frame, the distance between the pupil and the bottom edge of the frame.

A further object of the invention is a device of this kind which produces directly usable digital data.

SUMMARY OF THE INVENTION

The invention consists in a device for measuring the ocular parameters of a subject, in particular the interpupillary distance, for the purpose of fitting a pair of spectacles, the device comprising a front panel, means on said front panel for establishing its position relative to the face of the subject, windows in said front panel corresponding to the positions of the lenses of a pair of spectacles to be fitted, optical means incorporating a convergent lens and having an optical axis normal to and centered on said front panel, means for adjusting the position of said convergent lens along said optical axis relative to an origin close to said front panel, a point source of light, an aiming hole optically coincident with said point source of light, said point source of light and said aiming hole being disposed on the opposite side of said front panel to said convergent lens and the focus thereof when at said origin, two graticules disposed in the plane of said front panel and each comprising at least one liquid crystal diascopic matrix with addressable lines and columns, means, incorporating digital address generating means, for adjusting the position of each graticule within the frame of a respective window and position indicators linked to said adjusting means.

Liquid crystal diascopic matrixes are substantially transparent when each point, defined by an address, receives no state change control signal. When a signal from an address generator is applied to a line or to a column, all points constituting the line or the column then change state, appearing to the observer as a horizontal or vertical straight line. The position of the line or the column corresponds to the digital control address, so that this address is a number representative of the ordinate or abscissae of the lines forming the graticule, in the coordinate system of the front panel. It will be understood that the digital signal generators can be controlled at high speed without loss of accuracy and that multiplication of the combinations of lines is achieved by switching circuits, without modifying the optical part of the graticules.

Each graticule preferably comprises a top matrix centered on the optical axis of one eye of an average subject and a bottom matrix centered at the level of the bottom edge of an average spectacle frame, and said adjusting means are preferably adapted to deliver line and column address signals to the top matrix and line address signals to the bottom matrix.

It will be understood that the top matrix determines the abscissa (column) and the ordinate (line) of the reflection of the point source on the cornea, whereas the bottom matrix determines the ordinate of the bottom edge of the frame surround. The combination of the column addresses of the two top matrixes is representative of the total interpupillary distance, whereas the combination of the line addresses of the two matrixes in the same set is representative of the appropriate distance between the optical center and the lower edge of the corresponding lens.

For preference, the adjusting means are adapted to deliver column address signals to the top matrix and line address signals to the top and bottom matrixes. This arrangement makes it easier to operate the device, by reducing the number of adjustments required in each measuring mode. Note that the adjustments relating to the top matrix are disturbed if the eyes of the subject cease temporarily to focus on the image of the point source. Also, the interpupillary distance is normally measured when the subject is not wearing the frame, as this measurement is more important and requires greater accuracy than measuring the position of the edge of the frame.

In a preferred arrangement, the display means are linked to the adjusting means and adapted to convert combinations of address signals into numbers representing ocular parameters. It will be clear that with the digital signals delivered by the address generators signifying the coordinates of specific points, it is a simple matter to determine by digital computation data usable for adapting lenses to a frame.

Other objects and advantages will appear from the following description of an example of the invention, when considered in connection with the accompanying drawings, and the novel features will be particularly pointed out in the appended claims.

BRIEF DESCRIPTION OF THE DRAWINGS

FIG. 4 is a block diagram showing the electronic control circuits of a device in accordance with the invention.

DESCRIPTION OF THE PREFERRED EMBODIMENT

Figure 1:
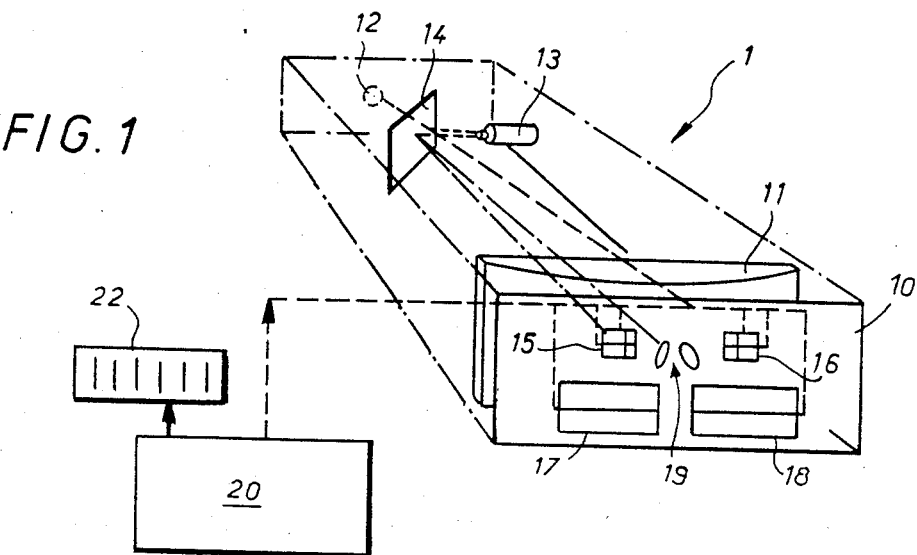
FIG. 1 is a general schematic of a device in accordance with the invention.

In the selected embodiment represented, a device for measuring ocular parameters comprises a parallelepipedal box 1 with a front panel 10 reproducing the front part of a spectacle frame, a plano-spherical lens 11 with its principal optical axis normal to the plane of the front panel 10 and adjustable in position along this principal optical axis, and an aiming hole 12 in the side of the box 1 opposite the front panel 10 and centered on the optical axis of the lens 11, the length of the box between the front panel 10 and the hole 12 being such that the focus of the lens 11 is at the center of the hole 12 when the lens is closest to the front panel 10.

A short distance in front of the hole there is disposed a partially reflecting mirror 14 oriented at substantially 45° to the optical axis. A compact light source 13 is disposed so that its image formed by reflection in the mirror 14 is coincident with the center of the hole 12.

The front panel 10 comprises means for establishing the position of the head of the subject whose ocular parameters are to be determined. These means comprise a pair of nose pads 19 and a forehead support (not shown) just above the top edge of the front panel 10. It will be understood that the nose pads 19 constitute a position indication corresponding to the nose pads of a conventional frame, whereas the forehead support ensures coincidence between the plane of the front panel and the mean front plane of the frame, incidentally ensuring coincidence between the vertical plane of symmetry of the front panel and the plane of symmetry of the head of the subject.

The front panel comprises windows 15, 16, 17 and 18 consisting of liquid crystal matrixes, as will be described in more detail hereinafter. The top windows 15 and 16 are square, with a side of approximately 16 millimeters, their centers being separated by the average interpupillary distance, which is approximately 60 millimeters. The bottom windows 17 and 18 are rectangular, with a height of approximately 27 millimeters and a width of approximately 50 millimeters, their centers being approximately 70 millimeters apart and about 43 millimeters from the line through the centers of the top windows 15 and 16, this being a typical value of the distance separating the optical center of a spectacle frame from its bottom edge. The edges of windows 15 to 18 are vertical and horizontal, and windows 15 and 17 are respectively symmetrical with windows 16 and 18 relative to the vertical center line of the front panel 10.

The liquid crystal matrixes comprise substantially square cells which are disposed in horizontal lines and vertical columns in such a way that it is possible to change the state of each point in the matrix by means of control signals addressed to the line and to the column which intersect at the cell in question.

However, in the ocular parameter measuring device, the control signals are adapted to change the state of all the cells in a line or in a column simultaneously. In practice, if the change in the state of a cell is commanded by a logic level "1", instead of applying a level of "+½" to the line and "−½" to the column, a "1" level is applied to the line or column which must change state.

The control circuits comprise a logic unit 20 selectively connected to the line and column inputs of the matrixes of windows 15 and 16 and to the line inputs of the matrixes of windows 17 and 18. A control keyboard 21 connected to the logic unit 20 constitutes, with the latter, a state change control address generator.

Each liquid crystal cell comprises a thin layer of birefringent nematic liquid between two transparent electrodes. Two appropriately oriented polarizing films are placed on respective sides of the matrix. When the cell is not receiving a state change control signal, the rotation of the plane of polarization induced by the nematic liquid crystal on the light between the polarizing films enables light to pass through the matrix; on the other hand, when the cell changes state this cancels the rotation of the plane of polarization between the two polarizing films. Looking through a cell, it appears opaque when "on" or transparent when "off". In the application to the ocular parameter measuring device described here, in which all the cells of a line or of a column change state simultaneously, the line or column appears as an opaque line contrasting with the remainder of the matrix which remains transparent. The way in which the change of state is commanded will be described later.

Figure 2:
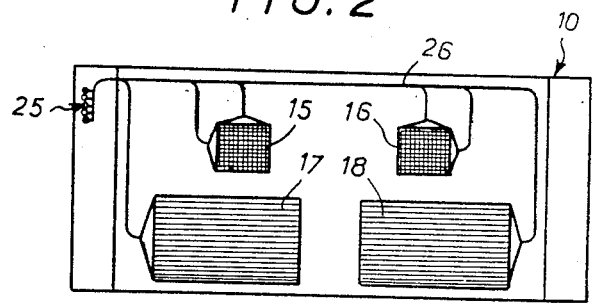
FIG. 2 is a more detailed view of a device front panel in accordance with the invention.

FIG. 2 is a more detailed view of the electro-optical structure of the front panel 10. Extending from a connector 25 is a bundle 26 of conductors which terminate at the line or column control connections to the matrixes of the top windows 15 and 16 and at the line control connections of the matrixes of windows 17 and 18. For reasons to be further explained later, in a first operating mode of the logic unit 20 (FIG. 1), the matrixes of the top windows 15 and 16 each receive a column state change control signal with an address determined by the keyboard 21 whereas, in a second operating mode, the matrixes of the four windows 15-18 each receive a line state change control signal with an address also determined by the keyboard 21, independently for each matrix. In the first mode, a dark vertical line appears in the top windows 15 and 16, and is adjustable in position, while in the second mode a dark horizontal line appears in each window, and is adjustable in position.

It will have been understood that, as with a conventional device for measuring the interpupillary distance, the subject to be fitted with a pair of spectacles places his face against the front panel 10 so that his pupils are in line with the top windows 15 and 16. The source 13 seen by reflection in the mirror 14 and by refraction through the lens 11, in the origin position close to the front panel 10, appears to the subject as a point at infinity and level with the horizon. The sight lines of the eyes of the subject are therefore parallel and in the "central" direction, that is to say straight ahead at horizon level. For the operator looking through the hole 12, the eyes of the subject appear as in a low-power magnifier, with a light spot at the center of the cornea, formed by the reflection of the source 13 on the convex surface of the cornea. Superimposed on this image are the dark lines corresponding to the columns or lines which have changed state in the matrixes of the top windows 15 and 16.

Figure 3A:
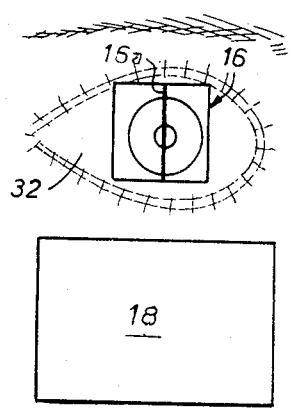
FIGS. 3A and 3B illustrate two stages of measurement using a device in accordance with the invention.
Figure 3B:
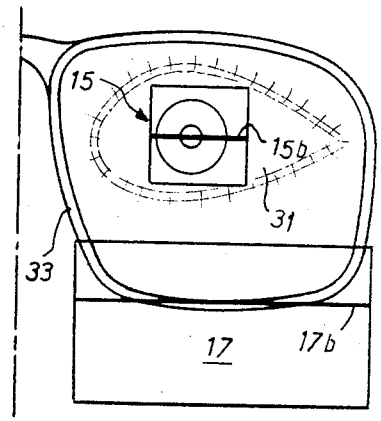

FIGS. 3A and 3B schematically represent the two operating modes, one being shown for the right eye and the other for the left eye, for reasons of convenience; it will have been understood that each mode applies to both eyes.

The first mode, FIG. 3A, is for measuring the interpupillary distance; only the matrixes of windows 15 and 16 receive signals, these being column address signals so that a dark vertical line 16a is seen. The address signals are modified using the keyboard 21 (FIG. 1) until the line 16a passes through the reflection of the light source on the cornea. Each address signal then corresponds to the distance from the center of the pupil of the corresponding eye to the vertical axis of symmetry of the front panel, and the sum of these distances is the interpupillary distance. The logic unit 20 (FIG. 1), which has a memory storing parameters defining the dimensions of the matrix and its position in the front panel, displays the interpupillary distance and the distances of the left and right pupils from the vertical axis of symmetry.

The second measuring mode, FIG. 3B, is for determining the position of the optical center of the lens in the frame; the matrixes of the four windows 15-18 receive line address signals resulting in the appearance of dark horizontal lines (15b in window 15, 17b in window 17). The measurement is carried out with the frame placed on the face of the subject; it will be clear that the nose pads 19 of the front panel 10, as shown in FIG. 1, are replaced by suitable bezels which appropriately position the frame 33 on the front panel. By means of the keyboard 21 (FIG. 1), the address signals are adjusted until the line 15b and the line 16b (not shown) pass through the center of the pupil of the corresponding eye 31; the line 17b and the line 18b (not shown) are adjusted in position to pass through the bottom edge of the frame. Taking into account the parameters defining the dimensions of the matrixes and their positions in the front panel, the combination of these signals provides for displaying the distance required between the optical center and the bottom edge of the lens for fitting it to the frame.

In the front panel 10 shown in FIG. 2, the matrixes of the top windows 15 and 16 have 64 lines and 64 columns in a square with 15.75 mm sides, with their inside edge 22 mm from the vertical axis of symmetry of the front panel. The points of the matrix measure 0.125×0.125 mm and are spaced by 0.125 mm. The matrixes of the bottom windows 17 and 18 measure 27×50 mm and comprise 55 lines 0.3 mm wide spaced by 0.2 mm. The inside edges of these matrixes 17, 18 are 10 mm from the bottom edges of the matrixes of the top windows 15 and 16.

FIG. 4 shows the configuration of the matrix control circuits. The heart of the control system consists of a microprocessor 50 which is connected to a control keyboard 51, a digital display device 52 and interface devices for direct control of the matrixes. The microprocessor 50 has an internal 2 MHz clock and is programmed so that the measurement modes succeed one another, the second beginning when the first is finished. The keyboard 51 incorporates address increase and decrease keys surmounted by a validation key, arranged as respective columns for the right and left eyes. Pressing the keys to increase or decrease the address signal moves the dark lines in the windows. When the alignment is correct, the validation key is pressed to enter the data into the microprocessor for computation of the values to be displayed. It will be understood that all this is achieved by the microprocessor's software.

For the formation of the address signals, successive addresses 1 to 64 are assigned to the lines of the top lefthand matrix, 65 to 128 to the columns of this matrix, 129 to 192 to lines of the top righthand matrix, 193 to 256 to the columns of this matrix, 257 to 311 to the lines of the bottom righthand matrix, and 312 to 366 to the lines of the bottom lefthand matrix. At the start of the microprocessor operating cycle, clock signals on microprocessor output 50a drive a succession of shift registers 60, 65, 70 each with a capacity of 32 cells, while signals appear on output 50b simultaneously with the clock pulses whose rank corresponds to the addresses of the matrix lines or columns to change state. On the 366th clock pulse the loading of shift registers 60, 65, 70 . . . , is completed and a load signal appears on output 50c of the microprocessor 50, synchronized with the 367th clock pulse. The load circuits 61, 66, 71 . . . , placed between the shift registers 60, 65, 70 . . . , and the state change controllers 62, 67, 72 . . . , connected to the lines and columns of the liquid crystal matrixes, transfer the contents of registers 60, 65, 70 . . . , to the controllers 62, 67, 72 . . . . The controllers 62, 67, 72 . . . have a capacity of 32 lines or columns, but those which are connected to the lines of the bottom matrixes have only 22 or 23 outputs used. The controllers receive a bias signal at 200 Hz provided by the generator 53 connected to the microprocessor 50 which is transmitted to the lines and columns in accordance with the address signal transmitted by the load circuits. The complete microprocessor cycle lasts from 30 to 50 ms, corresponding to correct operation of the liquid crystals, given their inertia to changing state. However, the loading of the shift registers, during which the microprocessor is assigned to address generation, lasts only 183 microseconds.

The shift registers 60, 65, 70, the load circuits 61, 66, 71 and the controllers 62, 67, 72 are commercially available integrated circuits in widespread use, in particular for controlling liquid crystals. Thus there is no requirement to go into their individual operation at length.

It will be obvious that the measurement results indicated by the display 52 may be passed to a printer to print out a data sheet for finishing machining of lenses to fit them to the frame.

Note that the expression "window", which of itself suggests an opening in a wall intended to allow light to pass, must not be understood in too narrow a sense in the present description, that is to say as indicating that the parts of the front panel other than these windows are opaque. In accordance with the invention, these parts could just as well be transparent as opaque.

It is no less evident that the bottom matrixes could consist of a single column, the lines extending in a parallel array across the full width of the window.

It will also be clear that the liquid crystal matrixes could be controlled on a point-to-point basis, each point having its own individual control input. In such a case, they would be associated with control interfaces capable of sending to the necessary points individual control signals conditioned by the line and column address signals.

It will be understood that various changes in the details, materials and arrangements of parts, which have been herein described and illustrated in order to explain the nature of the invention, may be made by those skilled in the art within the principle and scope of the invention as expressed in the appended claims.

It is claimed:

1. A device for measuring the ocular parameters of a subject, in particular the interpupillary distance, for the purpose of fitting a pair of spectacles, the device comprising a front panel, means on said front panel for establishing its position relative to the face of the subject, windows in said front panel corresponding to the positions of the lenses of a pair of spectacles to be fitted, optical means incorporating a convergent lens and having an optical axis normal to and centered on said front panel, means for adjusting the position of said convergent lens along said optical axis relative to an origin close to said front panel, a point source of light, an aiming hole optically coincident with said point source of light, said point source of light and said aiming hole being disposed on a side of said convergent lens opposite to said front panel and on the focus of said convergent lens when at said origin to said front panel, two graticules disposed in the plane of said front panel and each comprising at least one liquid crystal diascopic matrix with addressable lines and columns, means, incorporating digital address generating means, for adjusting the position of each graticule within the frame of a respective window and position indicators linked to said adjusting means.

2. A device according to claim 1, wherein each graticule comprises a top matrix centered on the optical axis of one eye of an average subject and a bottom matrix centered at the level of the bottom edge of an average spectacle frame, and said adjusting means are adapted to deliver line and column address signals to the top matrix and line address signals to the bottom matrix.

3. A device according to claim 2, wherein said adjusting means are adapted to deliver column address signals to the top matrix or line address signals to the top and bottom matrixes.

4. A device according to claim 1, wherein said graticules are linked to said adjusting means and are adapted to convert combinations of address signals into numbers representing ocular parameters.

* * * * *